(12) United States Patent
Raines et al.

(10) Patent No.: US 7,932,239 B2
(45) Date of Patent: Apr. 26, 2011

(54) METHODS OF AND COMPOSITIONS FOR REDUCING NEURONAL CELL DEATH

(75) Inventors: Ronald T. Raines, Madison, WI (US); Leonard A. Levin, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1342 days.

(21) Appl. No.: 11/412,353

(22) Filed: Apr. 27, 2006

(65) Prior Publication Data

US 2006/0258622 A1    Nov. 16, 2006

Related U.S. Application Data

(60) Provisional application No. 60/675,835, filed on Apr. 28, 2005.

(51) Int. Cl.
| | |
|---|---|
| *A01N 55/08* | (2006.01) |
| *A01N 57/00* | (2006.01) |
| *A61K 31/69* | (2006.01) |
| *A61K 31/66* | (2006.01) |
| *C07F 5/02* | (2006.01) |
| *C07F 9/02* | (2006.01) |

(52) U.S. Cl. ............... 514/64; 514/75; 514/120; 568/2; 568/6; 568/8; 568/13; 568/17

(58) Field of Classification Search .......... 514/64, 514/75, 120; 568/2, 6, 8, 13, 17
See application file for complete search history.

(56) References Cited

U.S. PATENT DOCUMENTS 6,706,926 B1    3/2004    Brown et al.

OTHER PUBLICATIONS

Imamoto et al. 1990, Synthesis and Reactions of phosphine-boranes. J. Am. Chem. Soc. vol. 112, pp. 5244-5252.*
Gourdel et al. 1993, Activation of Phosphines with borane. Tetrahedron Letters, vol. 34, No. 6, pp. 1011-1012.*
Leautey et al. 2001, Synthesis of alpha-substituted beta-amidophosphines by diastereoselective alkylation. J. Org. Chem. vol. 66, No. 16, pp. 5566-5571.*
Cheng C, et al., "Intravitreal sustained-release dexamethasone device in the treatment of experimental uveitis," Invest. Opthalmol. Vis. Sci. 36:442-453 (1995).
Chetoni P, et al., "Ocular mini-tablets for controlled release of timolol: evaluation in rabbits," J. Ocul. Pharmacol. Ther. 129:245-252 (1996).
Feist R, et al., "Effectiveness of apraclonidine and acetazolamide in preventing postoperative intraocular pressure spikes after extracapsular cataract extraction," J. Cataract Refract. Surg. 21:191-195 (1995).
Geiger L, et al., "Reduced redox state allows prolonged survival of axotomized neonatal retinal ganglion cells," Neuroscience 109:635-642 (2002).
Imamoto T, et al., "Phosphine oxides and lithium aluminum hydride-sodium borohydride-cerium(III) chloride: synthesis and reactions of phosphine-boranes" J. Am. Chem. Soc. 107:5301-5303 (1985).
Imamoto T, "Synthesis and reactions of new phospine-boranes," Pure & Appl.Chem. 65:655-660 (1993).
Joshi A, "Microparticulates for ophthalmic drug delivery," J. Ocul. Pharmacol. 10:29-45 (1994).
Levkovitch-Verbin H, et al., "Translimbal laser photocoagulation to the trabecular meshwork as a model of glaucoma in rats," Invest. Ophthalmol. Vis. Sci. 43:402-410 (2002).
McCalden T & Levy M, "Retention of topical liposomal formulations on the cornea," Experientia 46:713-715 (1990).
Meseguer G, et al., "Gamma scintigraphic comparison of eyedrops containing pilocarpine in healthy volunteers," J. Ocular. Pharm. Ther. 12:481-488 (1996).
Nelson M, et al., "Ocular tolerability of timolol in Gelrite in young glaucoma patients," J. Am. Optom. Assoc. 67:659-663 (1996).
Rampal J, et al., "Carbon-phosphorus heterocycles. Synthesis and conformational analysis of alkyl-substituted 1,2,6-triphenyl-4-phosphorinanones and derivatives," J Am. Chem. Soc. 46:1166-1172 (1981).

* cited by examiner

*Primary Examiner* — Sreeni Padmanabhan
*Assistant Examiner* — Kara R McMillian
(74) *Attorney, Agent, or Firm* — Quarles & Brady LLP

(57) ABSTRACT

Methods and compositions involving a class of boron-protected phenylphosphine agents having increased cell permeability and having improved chemical stability for treating or for preventing neuronal cell death-related diseases or conditions in a human or a non-human animal.

9 Claims, 7 Drawing Sheets

A 2-(Diphenylphosphino)benzoic acid
(2DPBA)

B 4-(Diphenylphosphino)benzoic acid
(4DPBA)

C 3,3',3''-Phosphinidynetris(benzene-
sulfonic acid), trisodium salt
(3BSA)

METHODS OF AND COMPOSITIONS FOR REDUCING NEURONAL CELL DEATH

CROSS-REFERENCE TO RELATED APPLICATIONS

This application claims the benefit of U.S. Provisional Patent Application No. 60/675,835, filed Apr. 28, 2005, incorporated herein by reference as if set forth in its entirety.

STATEMENT REGARDING FEDERALLY SPONSORED RESEARCH OR DEVELOPMENT

This invention was made with United States government support awarded by the following agency: NIH EY012492. The United States has certain rights in this invention.

BACKGROUND

Neuronal cell death is a final pathway common to a variety of diseases including neurodegenerative disorders and ophthalmological disorders, such as glaucoma, that involve injury to retinal ganglion cells (RGCs). In glaucoma, an increase in intraocular pressure (IOP) damages RGCs, causing them to undergo apoptosis. Consequently, vision is irreversibly lost.

The exact mechanism by which neuronal cells undergo apoptosis in various neurodegenerative and ophthalmological disorders has not been unequivocally established. In the case of axonal injury-induced RGC apoptosis, it is speculated that blockage of retrograde axonal transport of neutrophins and/or production of an injury signal are contributing factors.

There is considerable interest in the art in identifying/developing molecules that can reduce neuronal cell death. In this regard, tris-(2-carboxyethyl) phosphine (TCEP) has been reported to reduce axonal injury-induced RGC apoptosis. Geiger et al., Neuroscience 109:635-642 (2002).

BRIEF SUMMARY

In one aspect, the present invention is summarized in that a method for protecting neuronal cells from cell death includes the step of exposing one or more neuronal cells to an effective amount of one or more compounds having the formula:

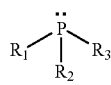

(Formula I)

wherein $R_1$ to $R_3$ are identical or different and represent a carbon chain of one to thirty carbons, preferably one to twenty or one to ten carbons, and most preferably one to eight, two to seven, or three to six carbons; the carbon chain can be saturated, unsaturated, linear, branched, cyclic or polycyclic, and can have heteroatoms, such as F, Cl, Br, I, O, S, P and N, and preferably O, attached as part of the chain or of a side group.

The above compounds also include pharmaceutically acceptable salts thereof. Specifically excluded from the method of the present invention is the use of TCEP.

In some embodiments, at least one of $R_1$ to $R_3$ of Formula I is an aryl group (e.g. a phenyl group) or a substituted aryl group (e.g. a substituted phenyl group), at least one of $R_1$ to $R_3$ is an alkyl ester group (R—C(O)—O—R', either R or R' can be attached to P), or both. In other embodiments, the aromatic ring of the aryl or substituted aryl group is directly linked to the phosphorus.

In preferred embodiments, the lone pair of electrons on the phosphorus of Formula I is protected by a removable protective group $R_4$ (Formula II) such as H or $BH_3$. In more preferred embodiments, the lone pair of electrons is protected by $BH_3$.

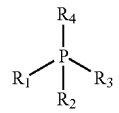

(Formula II)

In other embodiments, $R_1$ to $R_3$ of Formula I are selected from an aryl group (e.g., a phenyl group), a substituted aryl group (e.g., a substituted phenyl group) and an alkyl ester group, wherein at least one of $R_1$ to $R_3$ is an aryl or substituted aryl group and at least one of $R_1$ to $R_3$ is an alkyl ester group. In preferred embodiments, the lone pair of electrons are protected by $BH_3$. In more preferred embodiments, the compounds defined by Formula I are bis(3-propionic acid methyl ester)phenylphosphine borane comlex (PB1) and (3-propionic acid methyl ester)diphenylphosphine borane complex (PB2), described in detail below.

In some embodiments, the method of the present invention is employed to protect neuronal cells of a mammalian species such as human or rat neuronal cells. In preferred embodiments, a specific type of neuronal cells—RGCs—are protected In a second aspect, the PB2 compound and a pharmaceutical composition comprising the compound and a pharmaceutically acceptable carrier are also within the scope of the present invention.

The previously described embodiments of the present invention have many advantages, including a first advantage that the compounds protect neuronal cells in vitro, as well as in vivo.

It is a second advantage that the methods and compounds are useful in enhancing survival and viability of neuronal tissue used in transplants.

It is a third advantage that the compounds may be applied topically.

It is a fourth advantage that the compounds possess antioxidant properties and may therefore be used to protect against oxidative damage.

These and other features, aspects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the appended claims for interpreting the scope of the invention

BRIEF DESCRIPTION OF THE DRAWINGS

The invention will be better understood and features, aspects and advantages other than those set forth above will become apparent when consideration is given to the following detailed description thereof. Such detailed description makes reference to the following drawings, wherein.

Figure 1:
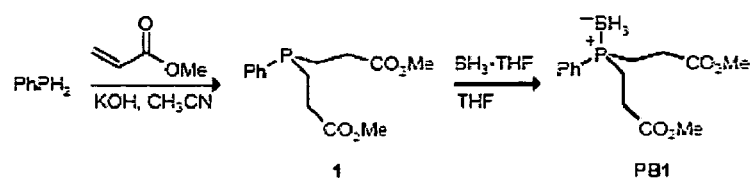
FIG. 1 shows a PB1 synthesis pathway.

The present invention is not intended to be limited to any particular operative theory; alternative or additional mechanisms of action, such as reducing other thiol modifications, scavenging of superoxide, and reducing other molecules, are certainly possible.

DESCRIPTION OF PREFERRED EMBODIMENTS

Unless defined otherwise, all technical and scientific terms used herein have the same meaning as commonly understood by one of ordinary skill in the art to which the invention belongs. Although any methods and materials similar to or equivalent to those described herein can be used in the practice or in the testing of the present invention, the preferred methods and materials are now described As used herein, the term "neuronal cells" encompasses any differentiated neuronal cells such as neurons (e.g. RGCs) or glial cells (e.g., astrocytes and oligodendrocytes) of either the central or the peripheral nervous system. The term also encompasses neuronal stem cells and neuronal progenitor cells. Neuronal cells encompassed by the term can assume any form such as the form of a tissue or dissociated neuronal cells (e.g. in a cell suspension).

As used herein, the term "cell death" encompasses apoptosis, necrosis and other types of cell death, such as mixed type of cell death.

As used herein, an "effective amount" of one or more compounds means an amount effective to protect neuronal cells from cell death. For the purpose of the present invention, the protective effect of a compound can be measured, for example, by a longer cell survival time, a decrease in the percentage of cells that die within a particular period of time or both in compound-treated cells in comparison to control cells. Of course, what constitutes the effective amount will depend on a variety of factors, including, for example, the size, the age and the condition of the individual, as well as on the mode of delivery. It is well within the ability of one of ordinary skill in the art to determine the effective amount.

The compounds of the present invention can protect neuronal cells both in vitro (e.g. in cultured cells) and in vivo (e.g. in a human or in a non-human animal). For example, protective compounds may be used with cultured neuronal cells or with tissue maintained ex vivo for purposes of transplantation into one or more sites in the eye of a patient suffering from an optic neuropathy. In this instance, the protective compound would enhance survival and viability of the neural tissue and increase the chances of a successful graft. Use of protective compounds in this context can be achieved with any of the available culturing or grafting procedures.

For in vivo applications, the compounds of the present invention are used to treat a subject (e.g., a patient) who is experiencing a neuronal cell death-related disease or condition. The compounds can also be used to prevent the disease or the condition (including partial prevention such as delay and minimizing symptoms at onset of disease or condition) in an at-risk individual not yet showing signs of the disease or the condition. In these applications, one or more compounds of the present invention are administered to a subject in an effective amount to treat or to prevent the disease or the condition.

Examples of neuronal cell death-related diseases or conditions that can be treated or can be prevented include, but are not limited to various neurodegenerative disorders (e.g. Alzheimer's disease, Huntington's Disease, prion diseases, Parkinson's Disease, amyotrophic lateral sclerosis, ataxia telangiectasia, spinobulbar atrophy, age-related reduction in number or in function, macular degeneration, retinal degeneration, dominant optic atrophy and Leber's hereditary optic neuropathy), diseases and conditions induced under various conditions of ischemia and/or excitotoxicity (e.g. ischemic stroke, hemorrhagic stroke and ischemic optic neuropathy), diseases due to nervous system trauma (e.g. spinal cord injury or traumatic optic neuropathy), diseases due to inflammation (e.g. optic neuritis or multiple sclerosis), diseases due to infection (e.g. meningitis and toxoplasmosis optic neuropathy), diseases and conditions induced by certain medications or irrigating solutions (e.g. optic neuropathy induced by ethambutol or methanol), and diseases due to other etiologies (e.g. glaucoma).

When the compounds of the present invention are used to protect neuronal cells in a subject in vivo, the compounds can be provided in a pharmaceutically acceptable carrier and can be administered to the subject via a topical or a systemic route, such as those described below.

In an exemplary embodiment, the compounds of the present invention are used to treat or to prevent a disorder related to neuronal cell death, including, but not limited to, glaucomatous optic neuropathy, ischemic optic neuropathy, inflammatory optic neuropathy, compressive optic neuropathy and traumatic optic neuropathy. In a preferred embodiment, the compounds of the present invention are used to treat or to prevent glaucoma.

It is reasonable to expect that the more neuronal cells that a protective compound contacts, the more pronounced its protective effect. Preferably, the method of the present invention allows a protective compound to contact at least about 25%, 50% or even as many as 95% or 100% of the cells.

Preferably, contacting the neuronal cells with one or more compounds of the present invention will reduce cell death by at least about 50% when compared to untreated cells. However, it is expected a reduction of cell death of 25%, 10% or 5% will extend the vision of the treated subject. In a human subject, a reduction in cell death may be estimated by extrapolation from functional and structural assays.

Functional assays involve evaluating changes in visual function over time, specifically, visual acuity and visual fields. It is reasonably expected that a reduction in the rate of neuronal cell death following initiation of treatment may be correlated with a reduction in the rate of loss of visual function over time. Structural assays involve visualizing or measuring the optic nerve head or the retinal nerve fiber layer with an ophthalmoscope or other device to assess optic disc atrophy, disc cupping or loss of nerve fibers.

A protective compound can be made to target a neuronal cell, such as a RGC, by linking it to an antibody or other molecule that can bind a cell surface antigen, such as Thy-1, which is a major RCG cell surface protein. For example, a protective compound can be covalently linked to a cell-specific aptamer. The Systematic Evolution of Ligands by EXponential enrichment (SELEX) procedure can be used to produce RNA molecules that bind to Thy-1. See Tuerk C & Gold L, Science 249:505-510 (1990), incorporated herein by reference as if set forth in its entirety. A library of RNA molecules can be generated by in vitro transcription from a commercially generated DNA library of sequences having a combinatorially rich random nucleotides core flanked by primer binding sequences (e.g., FFFFFFFFFFFFFFFFNNNNNNNNNNNRRRRRRRRRR RRRR, wherein FFFFFFFFFFFFFFFF represents a binding site for a forward primer, wherein RRRRRRRRRRRRRRRR represents a binding site for a reverse primer, and wherein NNNNNNNNNN is twenty-four to thirty-six combinatorially rich random nucleotides). Purified Thy-1 can then be attached to sepharose beads, the RNA molecules allowed to bind, the beads washed, and the bound RNA eluted. The eluted RNAs are molecules with increased affinity for Thy-1. They can then be reverse transcribed and amplified in a PCR reaction (using the forward and the reverse primers that bind to all of the molecules). The amplimers will then be transcribed, and the process repeated. The optimal RNA sequences are then synthesized with resistant nucleotides and covalently attached to a protective compound.

For treating a neuronal cell death-related disorder, protective compounds may be administered singly or in combinations of two or more protective compounds, with or without other active drugs, including without limitation, ocular hypotensive and other anti-glaucoma agents (e.g. prostaglandins or prostanoids, carbonic anhydrase inhibitors, beta-adrenergic agonists and antagonists, alpha-adrenergic agonists, N-acetyl cysteine, glutathione or other anti-glaucoma agents) known to those skilled in the art. Protective compounds may be delivered within any appropriate pharmaceutical formulation by topically (e.g. eye drops), transclerally, intravitreally, intraorbitally (e.g. retrobulbar or peribulbar injection), subconjunctivally, orally, intravenously, subcutaneously, intramuscularly, intraocularly, transdermally, bucally, intravaginally, rectally, nasally, intracerebrally, intraspinally or any of a variety of novel alternative drug delivery systems including those currently marketed, or any other means that is appropriate to the compound(s) in question.

For easy access to neuronal cells, protective compounds can be delivered through injection or depot injection in or around the vitreous, the retinal nerve fiber layer, the optic nerve fibers or the targets of neuronal cells within the brain. Topical ophthalmic compositions are employed when the compounds are to be dosed topically. Preferably, the topically dosed compounds are formulated for sustained release over a period of time. See Remington's Pharmaceutical Sciences (14th Ed. 1970); Joshi J, Ocul. Pharmacol. 10:29-45 (1994); McCalden et al., Experientia 46:713-715 (1990); Feist et al., J. Cataract Refract. Surg. 21:191-195 (1995); Cheng et al., Invest. Opthalmol. Vis. Sci. 36:442-453 (1995); and Chetoni et al., J. Ocul. Pharmacol. Ther. 129:245-252 (1996), each of which is incorporated herein by reference as if set forth in its entirety. Also preferably, the topically dosed compounds are formulated to increase penetration and to increase corneal contact time. See Meseguer et al., J. Ocular. Pharm. Ther. 12:481-488 (1996); and Nelson et al., J. Am. Optom. Assoc. 67:659-663 (1996), each of which is incorporated herein by reference as if set forth in its entirety.

The preparation of topical ophthalmic compositions is well known in the art. Generally, topical ophthalmic compositions useful in the present invention are in the form of a solution, a suspension, a gel or formulated as part of a device, such as a collagen shield or other bioerodible or non-bioerodible device.

Various excipients may be contained in the topical ophthalmic solutions, suspensions or gels of the present invention. For example, buffers (e.g. borate, carbonate and phosphate), tonicity agents (e.g. sodium chloride, potassium chloride and polyols), preservatives (e.g. polyquaterniums, polybiguanides and BAS), chelating agents (e.g. EDTA), viscosity enhancing agents (e.g. polyethoxylated glycols) and solubility agents (e.g. polyethoxylated castor oils, including polyoxl-35 castor oil, Polysorbate 20, 60 and 80; Pluronic® F-68, F-84 and P-103; or cyclodextrin) may be included in the topical ophthalmic compositions.

Likewise, a variety of gels may be useful in topical ophthalmic gel compositions of the present invention, including, but not limited to, carbomers, polyvinyl alcohol-borate complexes, xanthan, gellan or guar gums.

Topical ophthalmic bioerodible and non-bioerodible devices (e.g. conjunctival implant) may be used for topical administration of protective compounds. See Weiner A, "Polymeric Drug Delivery Systems For the Eye," in Polymeric Site-Specific Pharmacotherapy, (A. J. Domb, Ed., John Wiley & Sons, pp. 316-327, 1994). Topical administration is suitable for facilitating the delivery of the protective compounds described herein to enable chronic treatment of the eye.

Protective compounds may also be delivered on a solid or a semisolid scaffold, wherein delivery is accomplished by placing the support in a region of the eye selected from the group consisting of an eyelid, a conjunctiva, a sclera, a vitreous, a retina, an optic nerve sheath, an intraocular location and an intraorbital location. Additionally, protective compounds may be delivered slowly over time to the eye through the use of contact lenses. This regimen is generally performed by first soaking the lenses in a protective compound and then applying the contact lenses to the eye.

When the protective compounds are administered during intraocular, intracerebral or intraspinal surgical procedures, such as through retrobulbar or periocular injection, intraocular perfusion or injection, or intraspinal or intracerebral injection or perfusion, the use of irrigating solutions as vehicles are most preferred. The most basic irrigating solutions generally comprise sterile saline or phosphate-buffered saline (PBS). More advanced irrigating solutions, however, are preferred. Also contemplated are sustained-release formulations.

As used herein, the term "physiologically balanced irrigating solution" refers to a solution adapted to maintain the physical structure and the function of tissues during invasive or noninvasive medical procedures. This type of solution typically contains electrolytes, such as sodium potassium, calcium, magnesium and/or chloride; an energy source, such as dextrose; and a bicarbonate buffer to maintain the pH of the solution at or near physiological levels. Various solutions of this type are known (e.g. Lactated Ringers Solution, BSS, RTM, BSS Plus RTM, Sterile Irrigating Solution and Sterile Intraocular Irrigating Solution).

Retrobulbar and periocular injections are useful techniques also known to those skilled in the art and are described in numerous publications including, for example, Ophthalmic Surgery: Principles of Practice, W. B. Sanders Co., Philadelphia, Pa., USA, pp. 85-87 (G. L. Spaeth, Ed., 1990).

Pharmaceutical compositions of the protective compounds can be formulated for systemic use using techniques well known in the art. Orally administered compositions are generally in the form of tablets, hard or soft gelatin capsules, suspension, granules, powders or other typical compositions and contain excipients typically present in such compositions. Methods for the preparation of such oral vehicles are well known by those skilled in the art. Parenterally administrated compositions are generally in the form of injectable solutions or suspensions. Methods for the preparation of such parenteral compositions are well-known by those skilled in the art.

It is appreciated that the compounds of the present invention are good electron donors (upon removal of the removable protective group if present), and thus have antioxidant activities. Accordingly, these compounds can be used to protect against oxidative damage to human or animal cells, tissues and organs in general. The role of reactive oxygen species (ROS) in the etiology of human diseases (e.g. cancer, atherosclerosis, rheumatoid arthritis, inflammatory bowel diseases, immune system dysfunctions, brain function decline and connective tissue dysfunction) is well-established.

Diseases and conditions caused by oxidative damage can be prevented or can be treated with the compounds of the present invention. The specifics on using these compounds for this purpose, such as the appropriate dosage and the route of administration, can be readily determined by a skilled artisan as described above in the context of protecting neuronal cell death-related diseases and conditions.

The invention will be more fully understood upon consideration of the following non-limiting examples.

EXAMPLES

Example 1

Neuroprotective Effects of Phosphine Compounds and Derivatives

Experimental Procedures

Animals: All experiments were performed in accordance with Association for Research in Vision and Ophthalmology (ARVO), institutional, federal and state guidelines regarding animal research.

Materials: Cell culture reagents were obtained from GIBCO (Grand Island, N.Y.). A retrograde fluorescent tracer, 4',6-diamidino-2-phenylindole (DAPI), and a fluorescent viability agent, calcein-AM, were obtained from Molecular Probes (Eugene, Oreg.). Papain was obtained from Worthington Biochemical (Freehold, N.J.). TCEP analogues bis(3-propionic acid methyl ester)phenylphosphine borane complex (PB1) and (3-propionic acid methyl ester) diphenylphosphine borane complex (PB2) were synthesized as described below. Unless noted, all other reagents were obtained from Sigma-Aldrich (St. Louis, Mo.).

RGC Labeling and Culture: RGCs were retrogradely labeled by stereotactic injection of the fluorescent tracer DAPI dissolved in dimethylformamide into the superior colliculi of anesthetized postnatal days two to four Long-Evans rats. DAPI binds to nuclear DNA and fluoresces under UV light. At postnatal days eleven to thirteen, the animals were sacrificed by decapitation, the eyes enucleated, and the retinas dissected in Hank's balanced salt solution (HBSS). After two incubations in enzyme solution containing papain (3.7 U/ml), each for 30 minutes at 37° C., the retinas were gently triturated with a Pasteur pipette and plated on poly-L-lysine-coated 96-well flat-bottomed tissue culture plates (0.32 cm$^2$ surface area/well) at a density of approximately 2000 cells/mm$^2$. The cells were cultured for 72 hours in Neurobasal-A, B27 supplement lacking antioxidants in a humidified 5% $CO_2$ incubator at 37° C.

Retinal Ganglion Cell Identification and Counting: RGCs were identified by the presence of DAPI, which appears blue when viewed with appropriate filters under epifluorescence. Cell viability was determined by metabolism of calcein-AM, which produces a green fluorescence when viewed with fluorescein filters. Cells were incubated in a 1 µM solution of calcein-AM in phosphate-buffered saline (PBS) for 30 minutes, after which the medium was replaced with fresh PBS. Wells were counted in duplicate or in triplicate.

Synthesis of PB1 and PB2: Chemicals and solvents were from Aldrich Chemical (Milwaukee, Wis.). Reactions were monitored by thin-layer chromatography and were visualized by ultraviolet light or staining with $I_2$. NMR spectra were obtained with a Bruker AC-300 or Varian Inova-600 spectrometer. Phosphorus-31 NMR spectra were proton-decoupled and referenced against an external standard of deuterated phosphoric acid. Mass spectra were obtained with electrospray ionization (ESI) or matrix-assisted laser desorption/ionization (MALDI) techniques.

Synthesis of bis(3-propionic acid methyl ester)phenylphosphine Borane Complex (PB1) (FIG. 1):

Phosphine 1: See Rampal et al., J Am. Chem. Soc. 103: 2032-2036 (1981), incorporated herein by reference as if set forth in its entirety. Phenylphosphine (10 g, 90 mmol) was dissolved in acetonitrile (10 ml, degassed) in a flame-dried, round bottom flask under Ar(g). Potassium hydroxide (1.0 N, 1.0 ml) was added to this mixture, and the resulting solution was cooled to 0° C. Methyl acrylate (16.2 ml, 180 mmol) was added at a rate that maintained the reaction temperature below 35° C. Upon complete addition of methyl acrylate, the reaction was heated at 50° C. for 8 hours. The reaction mixture was then washed with brine (2×10 ml). The organic layer was dried over $MgSO_4$(s), filtered, and concentrated en vacuo. The residue was purified by distillation with the desired product distilling at 160-170° C. (0.5 mm Hg). Phosphine 1 was isolated as a clear liquid (20.7 g, 73 mmol, 81% yield).

Spectral data: $^1$H NMR (300 MHz, $CDCl_3$:$CD_3OD$) δ 7.54-7.48 (m, 2H), 7.37-7.30 (m, 3H), 3.62 (s, 6H), 2.46-2.23 (m, 4H), 2.10-2.03 (m, 4H) ppm; $^{13}$C NMR (75 MHz, THF-$d_6$) δ173.25 (d, J=12.9 Hz), 133.51 (d, J=15.5 Hz), 132.28 (d, J=19.4 Hz), 129.22, 128.43 (d, J=7.2 Hz), 51.47, 30.22 (d, J=16.9 Hz), 22.63 (d, J=11.9 Hz) ppm; $^{31}$P NMR (121 MHz, $CDCl_3$:$CD_3OD$) δ−23.06 ppm; MS (ESI) m/z 305.0905 ($MNa^+$ [$C_{14}H_{19}O_4PNa^+$]=305.0919).

PB1: Phosphine 1 (20.7 g, 73 mmol) was dissolved in dry tetra hydro furan (THF) in a flame-dried round bottom flask under Ar(g). This solution was cooled to 0° C. and borane-THF (1.0 M in THF, 80.6 ml, 80.6 mmol) was added slowly. The reaction was stirred at 0° C. for 45 minutes and then was stirred at room temperature for an additional 1.5 hours. The solvent was removed under reduced pressure, and the residue was purified by flash chromatography (silica gel, 80% v/v methylene chloride in hexanes). PB1 was isolated as a clear oil (7.6 g, 25.6 mmol, 35% yield).

Spectral data: $^1$H NMR (300 MHz, $CDCl_3$:$CD_3OD$) δ 7.78-7.70 (m, 2H), 7.57-7.47 (m, 3H), 3.64 (s, 6H), 2.70-2.56 (m, 2H), 2.41-2.19 (m, 6H), 0.68 (m, 3H) ppm; $^{13}$C NMR (75 MHz, THF-$d_6$) δ172.29 (d, J=19.1 Hz), 131.88 (d, J=13.5 Hz), 131.84, 128.93 (d, J=12.3 Hz), 126.11 (d, J=61.4 Hz), 51.83, 27.37, 20.71 (d, J=45.4 Hz) ppm; $^{31}$P NMR (121 MHz, $CDCl_3$:$CD_3OD$) δ17.34 (d, J=70.4 Hz) ppm; MS (ESI) m/z 318.1292 ($MNa^+$ [$C_{14}H_{22}BO_4PNa^+$]=318.1283).

Figure 2:
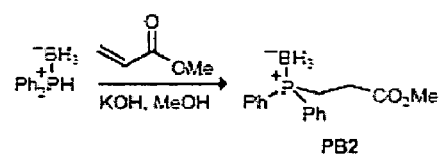
FIG. 2 shows a PB2 synthesis pathway.

Synthesis of (3-propionic acid methyl ester)diphenylphosphine Borane Complex (PB2) (FIG. 2):

PB2: See Imamoto et al., J. Am. Chem. Soc. 107:5301-5303 (1985), incorporated herein by reference as if set forth in its entirety. Borane-diphenylphosphine complex (0.190 g, 1.0 mmol) was dissolved in methanol (8 ml) in a flame-dried, round bottom flask under Ar(g) at room temperature. Potassium hydroxide (0.0028 g, 0.05 mmol) was added to this mixture, followed by the drop-wise addition of methyl acrylate (0.108 ml, 1.2 mmol). The reaction mixture was allowed to stir at room temperature for 6 hours, after which the methanol was removed en vacuo. The residue was taken up in dichloromethane (10 ml) and was washed with 0.5 N HCl (1×5 ml) and brine (1×5 ml). The aqueous layers were washed with dichloromethane (10 ml), and the combined organic layers were dried over $MgSO_4$(s), filtered and concentrated en vacuo. The residue was purified by flash chromatography (silica gel, 30% v/v ethyl acetate in hexanes). PB2 was isolated as a pale yellow oil (0.219 g, 0.76 mmol, 76% yield).

Spectral data: $^1$H NMR (300 MHz, $CDCl_3$) δ7.72-7.65 (m, 5H), 7.51-7.45 (m, 5H), 3.64 (s, 3H), 2.55 (m, 4H), 0.96 (m, 3H) ppm; $^{13}$C NMR (75 MHz, $CDCl_3$) δ132.37 (d, J=9.20 Hz), 131.67, 129.17 (d, J=10.1 Hz), 128.84, 52.24, 28.01, 21.15 (d, J=39.5 Hz) ppm; $^{31}$P NMR (121 MHz, $CDCl_3$) δ16.26 (d, J=59.0 Hz); MS (ESI) m/z 309.1190 ($MNa^+$ [$C_{16}H_{20}BO_2PNa^+$]=309.1192).

Statistical Analysis: All RGC viability calculations were normalized to the control (no treatment) condition by dividing the mean number of living RGCs in an experimental condition by the mean in controls. Comparisons were by unpaired t-test.

Results

Novel thiol-reducing agents PB1 and PB2 protect RGCs in vitro at very low concentrations: Previous studies have demonstrated that (1) a thiol-reducing agent, TCEP, potently prevented RGC death in vitro to a degree equivalent to the combined effect of brain-derived neurotrophic factor (BDNF) and ciliary neurotrophic factor (CNTF), and that (2) TCEP injected intravitreally into adult rats inhibited RGC death after optic nerve crush. The concentrations required for RGC neuroprotection with this molecule were on the order of 100 μM. The TCEP molecule, being highly polar, does not cross cell membranes well, and the extracellular stability of the compound is low.

Figure 3:
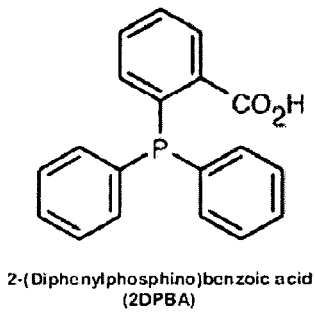
FIG. 3 shows mild neuroprotection by three tri-phenylated phosphino compounds. A dose-response analysis of 2-(diphenylphosphino)benzoic acid (2DPBA) yielded significant protection at 1 μM and 100 μM (A). Likewise, 4-(diphenylphosphino)benzoic acid (4DPBA) produced neuroprotection at 1 and 100 μM (B). Of the three tri-phenylated phosphines, 3,3',3"-phosphinidynetris(benzene-sulfonic acid) trisodium salt (3BSA) required the highest concentration (100 μM) to rescue RGCs from acute axotomy (C). RGCs were cultured at seventy-two hours in defined medium (see Example 1 below). All results were assessed at 72 hours using 4',6-diamidino-2-phenylindole (DAPI) for retrograde RGC labeling and calcein-AM staining for viability. An asterisk indicates $p<0.05$.
Figure 3:
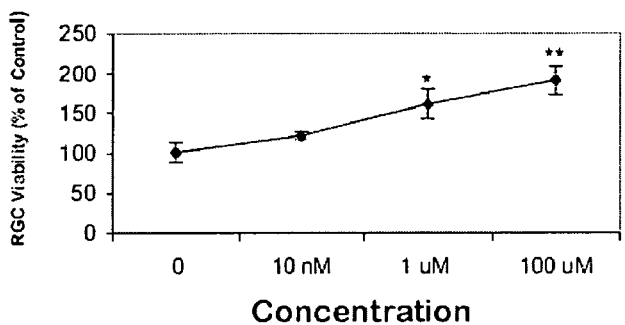
Figure 3:
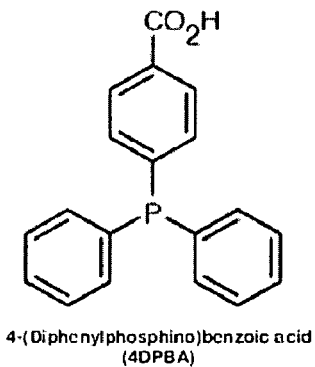
Figure 3:
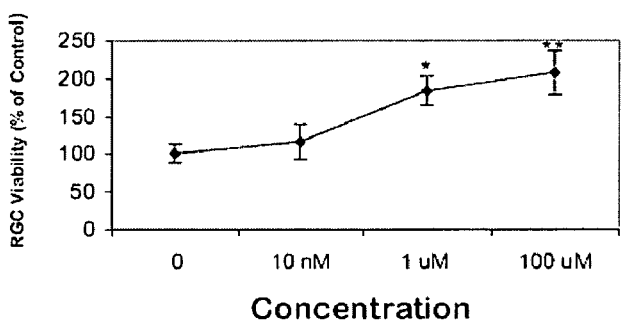
Figure 3:
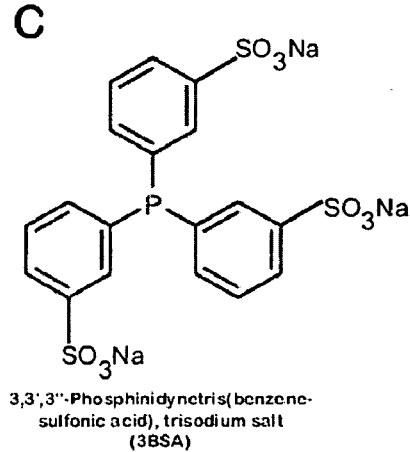
Figure 3:
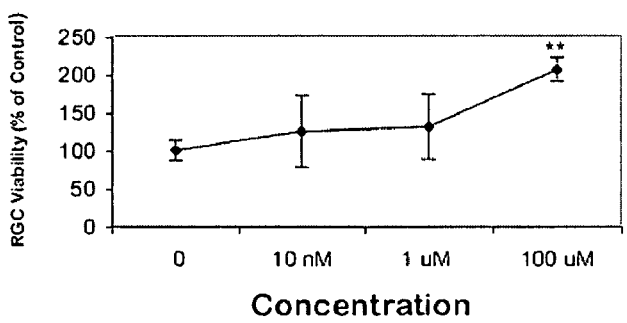

We tested the effects of three other phosphino compounds in vitro by using a standard method for postnatal day eleven to thirteen RGC culture, a time after which development of RGC death has already completed in the rat. Geiger et al., Neuroscience 109:635-642 (2002). 2DPBA prevented RGC death at concentrations as low as 10 nM (216±18%) at 72 hours. Additionally, 4DPBA rescued RGCs at 1 μM (183±19%), and 100 μM 3BSA increased survival (206±6%) (FIG. 3). The reduction potential of these phosphines prevents disulfide bond formation.

Figure 4:
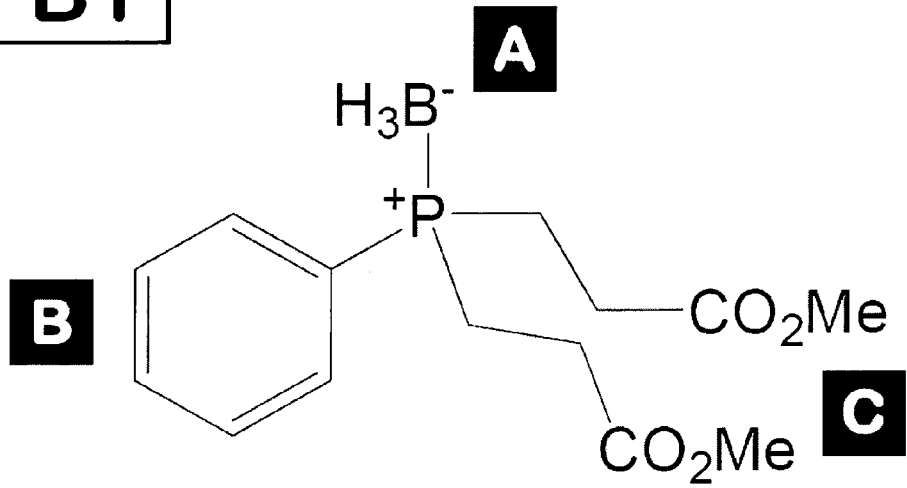
FIG. 4 shows the structure of PB1 and PB2. A borane protects the phosphine from oxidation, and thus stabilizes the molecule (A). The phenyl group is nonpolar (which is likely to increase the molecule's cell permeability), delocalizes the electron pair of the phosphino group by resonance and provides minimal steric hindrance (B). The methyl esters are likely cleaved by cytosolic esterases, resulting in an anionic molecule that is unlikely to exit the cytosol (C).
Figure 4:
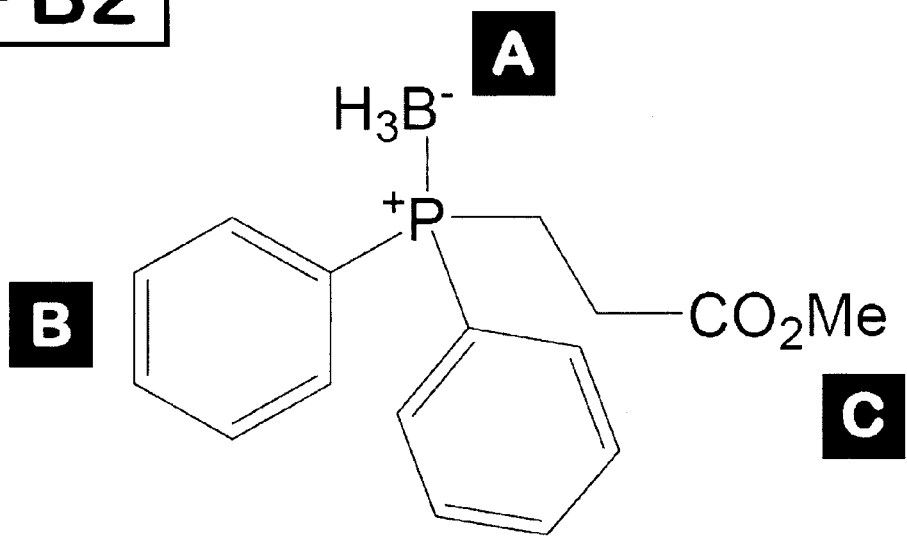
Figure 5:
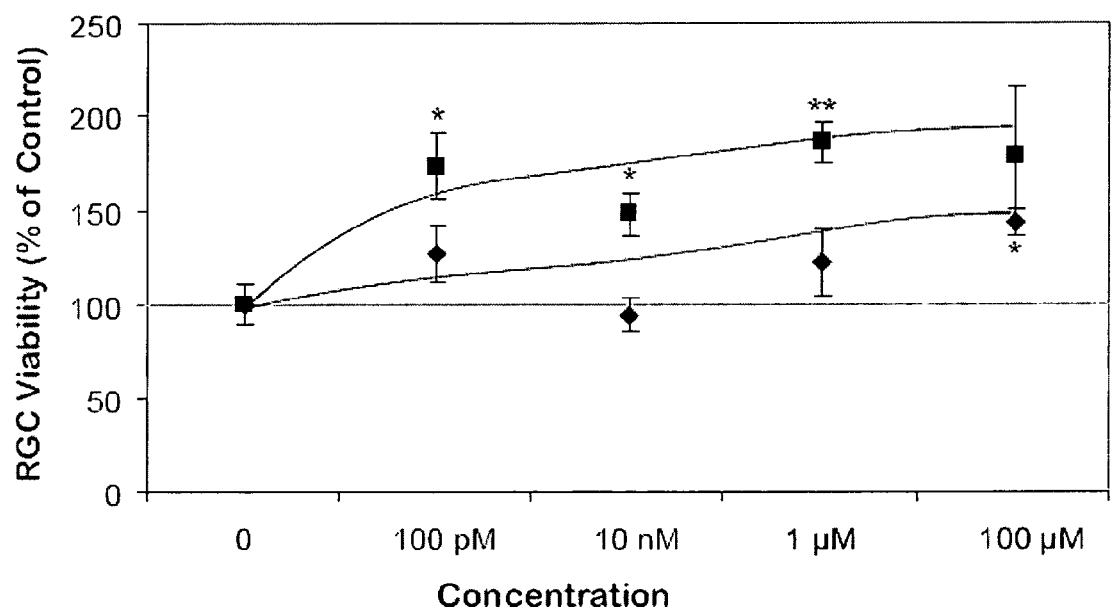
FIG. 5 shows that PB1 is neuroprotective at lower concentrations than TCEP. A dose-response curve of TCEP (diamonds) and PB1 (squares) was determined at 72 hours in vitro. TCEP mildly rescued RGCs at 100 μM, whereas PB1 was highly effective at picomolar concentrations. An asterisk indicates $p<0.05$, and a double-asterisk indicates $p<0.01$.
Figure 6:
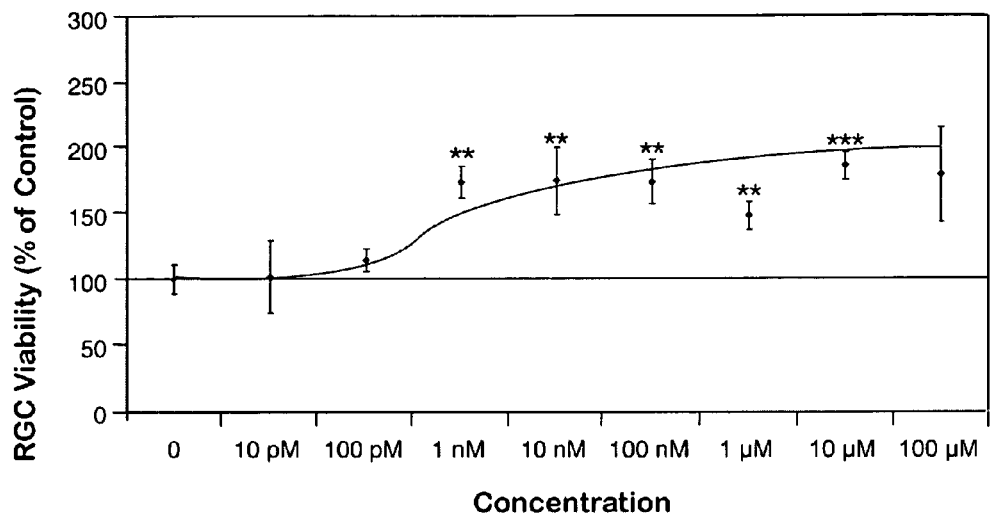
FIG. 6 shows that PB1 and PB2 are highly neuroprotective for axotomized RGCs at nanomolar and at picomolar concentrations, respectively. RGCs were cultured for seventy-two hours in defined medium, following which DAPI-positive RGCs were identified and calcein-AM staining was used to assess viability. Dose response curves of PB1 and PB2 ranging from 1 pM to 100 μM were assessed at 72 hours. PB1 was neuroprotective for RGCs at $\geq 1$ nM (A). PB2 was neuroprotective at $\geq 10$ pM (B). An asterisk indicates $p<0.05$, a double-asterisk indicates $p<0.01$, and a triple-asterisk indicates $p<0.001$.
Figure 6:
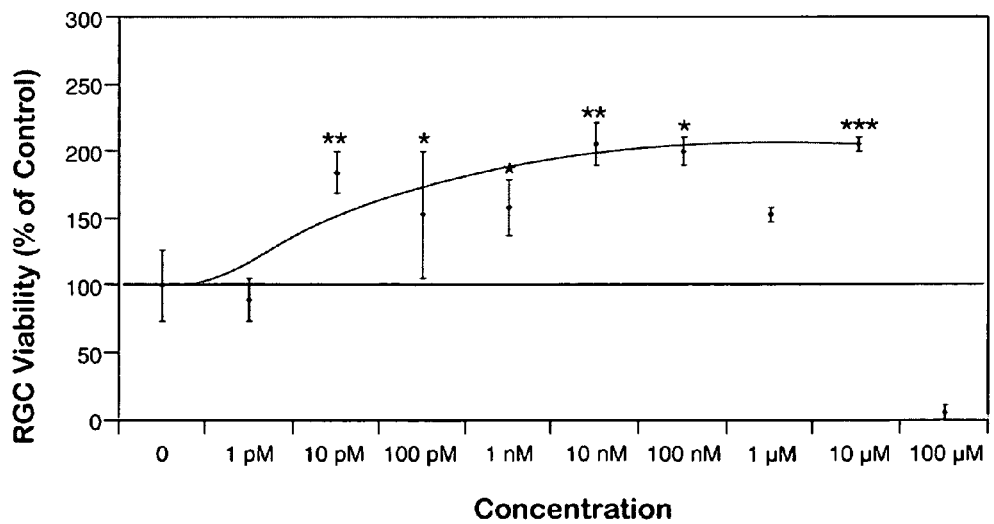

We further tested the neuroprotective effects of PB1 and PB2 (FIG. 4) in vitro. These two molecules were synthesized and then characterized by NMR spectroscopy and by mass spectrometry. As shown in FIG. 5, PB1 showed higher protection at lower concentrations than did TCEP at 72 hours after axotomy. Dose-response curves for PB1 and PB2 were generated over the range of 1 pM to 100 μM, and relative RGC survival (compared to control) was assayed at 72 hours after axotomy (FIG. 6). All data points were in duplicate or in triplicate, and all experiments were performed two to five times. PB1 rescued RGCs at concentrations as low as 1 nM (174±12%) at 72 hours; whereas PB2 increased RGC viability at 10 pM (180±10%) at 72 hours.

Figure 7:
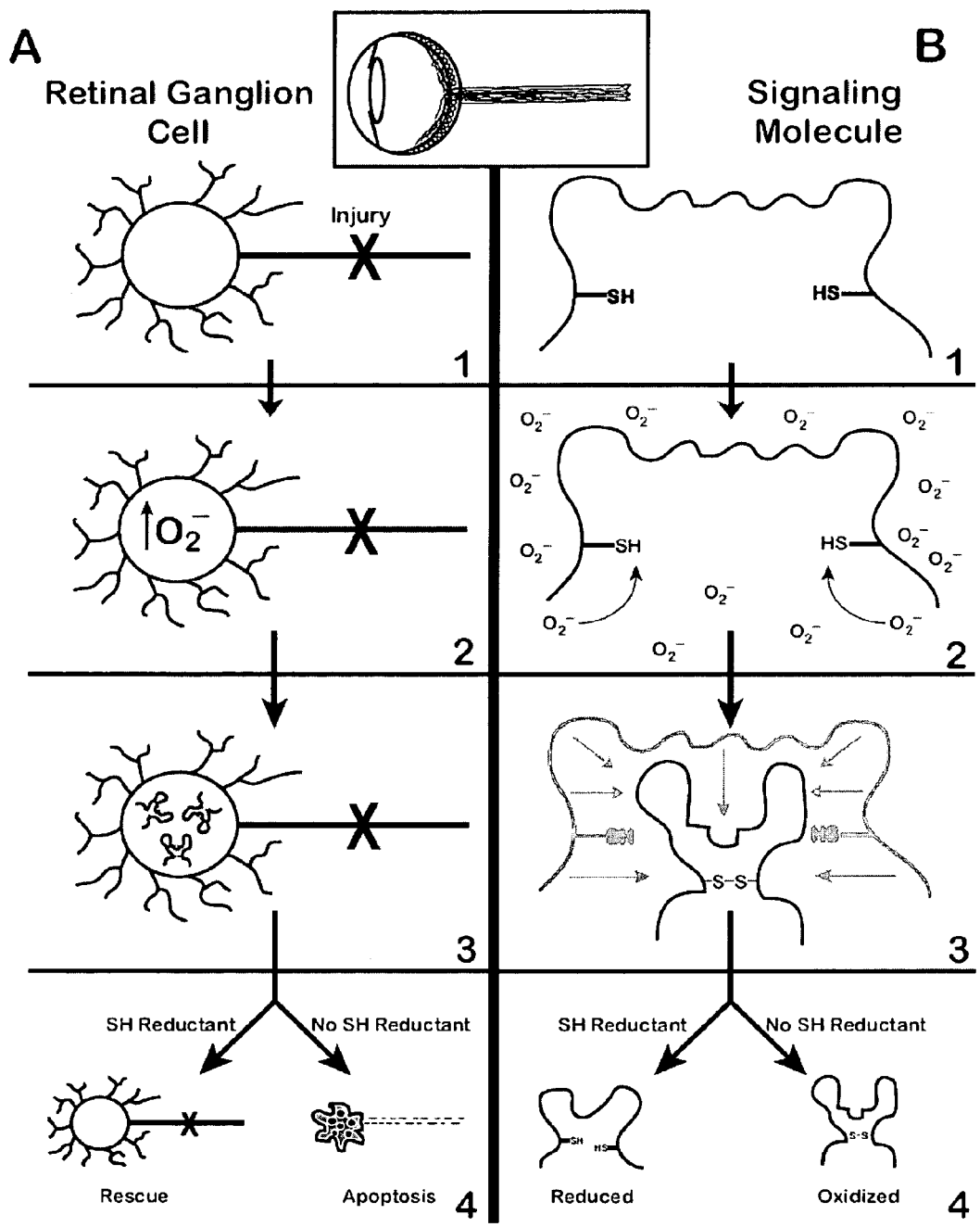
FIG. 7 is a schematic illustration of optic nerve injury and resultant protein modification via superoxide. RGC soma and axon are shown after injury ($A_1$-$A_4$) and corresponding conformational states of a hypothetical signaling protein ($B_1$-$B_4$) are also depicted. The inset displays a schematic drawing of the eye and of the optic nerve. A healthy RGC ($A_1$) contains a reduced signaling protein with free sulfhydryl groups (B1). Optic nerve injury or transection ($A_2$) initiates a rise in superoxide anion. Lievin et al., Invest. Ophthalmol. Vis. Sci. 47:1477-1485 (2006). Intracellular superoxide oxidizes the cysteine thiols of proteins ($B_2$). The concentration of superoxide increases over time within the RGC soma ($A_3$) and disulfide bonds are created as a result, inducing conformational changes and inducing apoptosis ($B_3$). The RGC will either undergo apoptosis (if untreated) or be rescued (if treated with thiol-reducing agents) ($A_4$). When a thiol-reducing agent, such as TCEP, PB1 or PB2, is administered, disulfide bonds are reduced, and the protein resumes normal conformation and function ($B_4$). Without the thiol-reducing agent, the signaling of apoptosis will continue.

In many optic neuropathies, injury to the nerve axon is believed to be the primary pathophysiological damage that initiates apoptosis (FIG. 7). After axotomy, a rise in ROS occurs, which is thought to be sufficient to be the upstream signaling event that induces the apoptotic cascade signal. Though the source of ROS has not been determined, our recent findings suggest that it may be partly generated in the mitochondrial electron transport chain. ROS induce oxidative stress within the cell and transduce signals by oxidizing reduced sulfhydryls. Cross J & Templeton D, J. Cell Biochem. 93:104-111 (2004). Disulfide bond formation within a protein or with other proteins alters its configuration, which can then prevent it from performing specific functions or cause it to initiate new reactions. Ultimately, the rise in ROS causes the cell to undergo an irreversible death cascade. The RGC can survive axotomy, however, if treated with thiol-reducing agents.

Previous studies have shown that other thiol-reducing agents, such as dithiothreitol (DTT) and TCEP, were not effective at nanomolar concentrations. Because these molecules are polar, they do not easily cross cell membranes and therefore required high extracellular concentrations to show any significant survival effects.

We have herein identified a class of reducing compounds that have neuroprotective activities. In particular, we found that the TCEP analogues PB1 and PB2 were highly neuroprotective at nanomolar and picomolar concentrations, respectively. Additionally, they were significantly more protective at lower concentrations than their predecessor, TCEP. Less protected phosphines, 2DPBA, 4DPBA and 3BSA were less effective at rescuing RGCs from acute axotomy. By modifying TCEP so that (1) its phosphino group can be protected from reaction in the extracellular milieu; and that (2) its pendant carboxyethyl groups were either replaced with a nonpolar phenyl group or converted to esters that can be cleaved by endogenous esterases within the RGC, we markedly increased the effectiveness of these compounds. Passage of PB1 and PB2 across the cell membrane and cleavage of their protective groups would produce highly effective thiol-reducing compounds. Because deprotected PB1 and PB2 are polar and highly charged, they will be confined within the RGCs. Accordingly, the phosphines can protect biomolecules from oxidation by ROS during optic nerve injury.

Example 2

Preventing RGC Death Associated with Optic Nerve Crush In Vivo

Experimental Procedures

Optic Nerve Crush Surgery and Intravitreal Injections: Surgeries are conducted on adult (i.e. eight to twelve week old) rats that have previously received 1,1'-dioctadecyl-3,3,3',3'-tetramethylindocarbocyanine (DiI) injections. All surgeries are done aseptically and are performed on the left eye only. Animals are anesthetized with a mixture of ketamine and xylazine. A limited lateral canthotomy is performed. The conjunctiva is then incised at the limbus and the subtenons space bluntly dissected posteriorly. Next, 4 μl of sterile drug (i.e. PB1 or PB2) or control (BSS) is slowly injected intravitreally just anterior to the pars plana using a 5 μl Hamilton syringe with a 33 gauge needle. Assuming the vitreous volume of an adult rat eye to be approximately 60 μl (Dureau et al., Curr. Eye Res. 22:74-77 (2001), incorporated herein by reference as if set forth in its entirety), this yields a seventeen-fold dilution from the injected concentration to the final intravitreal concentration of drug. The muscle cone is then entered and the optic nerve exposed. A longitudinal incision is made along the meningeal sheath to expose the optic nerve axons and to avoid disturbing the retinal blood supply. The axons of the optic nerve are then crushed with blunt forceps for 5 seconds 2 mm posterior to the globe under direct visualization. Complete interruption of the RGC axons is seen as a separation of the proximal and the distal optic nerve ends within the meningeal sheath. The skin is closed with absorbable suture and antibiotic ointment applied. The rats are given an intraperitoneal injection of buprenorphine (0.02 mg/kg) for analgesia and are returned to the cage. Rats with any kind of postoperative complication (e.g. cataract or retinal infarction) are excluded from analysis. Typically five to six animals are operated on at each sitting. To control for the effects of a test compound alone, some rats are injected with drug or with control without subsequent optic nerve crush. All animals are observed after recovering from anesthesia to ensure that they eat and drink normally.

Retinal Whole Mounts and BSL-I Staining: Seven to fourteen days after optic nerve crush and intravitreal injection (or intravitreal injection alone), the rats are euthanized with carbon dioxide. The eyes are rapidly enucleated, rinsed, punctured with a needle through the pupil and then fixed for 1 hour in 4% paraformaldehyde (PFA). The retinas are dissected, washed with PBS and then permeabilized in 0.2% Triton X-100 for 15 minutes. After another PBS wash, the retinas are stained with fluorescein-conjugated BSL-I (1:200) for two hours in order to label microglia, which can phagocytose DiI-containing apoptotic RGCs and thereby be confused with RGCs. See Shen et al., Neuron 23:285-295, (1999), incorporated herein by reference as if set forth in its entirety. The retinas are washed again and post-fixed with 4% PFA for 15 minutes. After a final wash, four cuts are made from the edge to the center of the retinas to flatten them. The flattened retinas are mounted with the RGCs facing up on glass slides in glycerol, and the coverslip is sealed with nail polish. The slides are stored in the dark at 4° C.

Results

RGC Density Determination: Retinal wholemounts are imaged with an Axiocarn HRc digital camera attached to a Zeiss Axiophot fluorescent microscope. Images are acquired using Axiovision 3.1 software. RGCs are identified by the presence of retrogradely transported cytoplasmic DiI. Fluorescein-conjugated BSL-I labeled cells appear green when viewed with fluorescein filters. The density of RGCs/mm$^2$ is determined by counting labeled DiI cells in three areas per retinal quadrant at three different eccentricities of the retinal radius for a total of twelve regions per retina. Cells positive for both DiI and BSL-I, as determined by bright yellow labeling when DiI (red) and BSL-I (green) images are merged, are subtracted from the total DiI count. An observer, masked to treatment or to the presence of optic nerve crush, performs the cell counts. A greater RGC density, reflecting reduced RGC death, is observed in animals administered PB1 or PB2 when compared to controls. Means are compared using a Student's unpaired t-test.

Example 3

Preventing RGC Death Associated with Ocular Hypertension In Vivo

Experimental Procedures

Unilateral experimental glaucoma is induced in the rat using the Quigley protocol for laser ablation of the trabecular meshwork and of the circumferential episcleral vessels. It causes steady RGC loss over a few weeks. See Levkovitch-Verbin et al., Invest. Ophthalmol. Vis. Sci. 43:402-410 (2002), incorporated herein by reference as if set forth in its entirety. The animals are anesthetized as in Example 2. A diode laser at 532 nm (0.2-0.4 watts and 0.3-0.7 second duration, depending on degree of pigmentation) is used to administer laser treatment at the trabecular meshwork and at the episcleral veins draining the perilimbal vessel plexus of vessel. In case a milder IOP rise is required, animals can be treated only at the trabecular meshwork. The laser treatment is repeated at 1 week if the IOP difference between the treated eye and the untreated eye is less than 6 mm Hg. Following laser treatment, sterile drug (i.e. PB1 or PB2) or control (BSS) is administered.

IOP is measured by putting a drop of 0.5% proparacaine in the eye, gently cradling the rat and touching the anesthetized eye with a Tonopen tonometer tip for a fraction of a second, usually for 3±2 times, more if the standard deviation is high. Tame Long-Evans rats typically do not require systemic anesthesia for this measurement procedure. Depending on the experiment, the IOP is initially measured daily and then weekly.

Results

After one to twelve weeks animals are sacrificed and RGC counts are performed as described in Example 2. RGC cell death is attenuated in animals administered PB1 or PB2 when compared to controls.

The invention has been described in connection with what are presently considered to be the most practical and the most preferred embodiments. However, the present invention has been presented by way of illustration and is not intended to be limited to the disclosed embodiments. Accordingly, those skilled in the art will realize that the invention is intended to encompass all modifications and alternative arrangements within the spirit and the scope of the invention as set forth in the appended claims.

We claim:

1. A method for protecting a neuronal cell from cell death, the method comprising the step of:

exposing one or more neuronal cells to an effective amount of a pharmaceutical composition comprising a compound having a formula of:

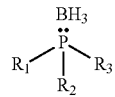

wherein two of $R_1$ to $R_3$ are aryl groups or substituted aryl groups and one of $R_1$-$R_3$ is $CH_2CH_2COOCH_3$; and a pharmaceutically acceptable carrier.

2. The method of claim 1, wherein the aryl group is a phenyl group and the substituted aryl group is a substituted phenyl group.

3. The method of claim 1, wherein the substituted aryl group comprises an aromatic ring directly linked to the phosphorus.

4. The method of claim 1, wherein the compound defined by the formula is (3-propionic acid methyl ester)diphenylphosphine borane complex.

5. The method of claim 1, wherein the neuronal cells are neurons.

6. The method of claim 5, wherein the neurons are retinal ganglion cells.

7. The method of claim 1, wherein the neuronal cells are human or non-human animal neuronal cells.

8. The method of claim 1, wherein the neuronal cells are protected in vivo in a human or in a non-human animal.

9. A pharmaceutical composition comprising:

a compound having a formula of:

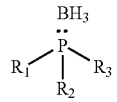

wherein two of $R_1$-$R_3$ are aryl groups or substituted aryl groups and one of $R_1$-$R_3$ is $CH_2CH_2COOCH_3$; and a pharmaceutically acceptable carrier.

* * * * *